US00RE40515E

(19) United States
(12) Reissued Patent
Kwun et al.

(10) Patent Number: US RE40,515 E
(45) Date of Reissued Patent: Sep. 23, 2008

(54) METHOD AND APPARATUS FOR INSPECTING PIPELINES FROM AN IN-LINE INSPECTION VEHICLE USING MAGNETOSTRICTIVE PROBES

(75) Inventors: Hegeon Kwun, San Antonio, TX (US); Sang Young Kim, San Antonio, TX (US)

(73) Assignee: Southwest Research Institute, San Antonio, TX (US)

(21) Appl. No.: 10/900,903

(22) Filed: Jul. 28, 2004

Related U.S. Patent Documents

Reissue of:
(64) Patent No.: 6,404,189
Issued: Jun. 11, 2002
Appl. No.: 09/738,062
Filed: Dec. 18, 2000

U.S. Applications:
(63) Continuation-in-part of application No. 09/519,530, filed as application No. PCT/US00/06359 on Feb. 25, 2000, now Pat. No. 6,294,912.
(60) Provisional application No. 60/124,763, filed on Mar. 17, 1999.

(51) Int. Cl.
*G01N 27/82* (2006.01)
*G01N 29/14* (2006.01)
*G01N 29/28* (2006.01)
*G01N 33/12* (2006.01)

(52) U.S. Cl. ..... 324/220; 324/240; 73/623; 73/643

(58) Field of Classification Search ..... 324/240, 324/340, 220; 73/623, 643
See application file for complete search history.

(56) References Cited

U.S. PATENT DOCUMENTS 4,055,990 A * 11/1977 Topping ..... 73/623
4,127,035 A * 11/1978 Vasile ..... 73/629
4,439,730 A 3/1984 Kaufman
4,769,598 A 9/1988 Krieg et al.
4,945,306 A 7/1990 Lowther (Continued)

FOREIGN PATENT DOCUMENTS

EP 0 304 053 A 2/1989
EP 0 389 877 A 10/1990

*Primary Examiner*—Reena Aurora
(74) *Attorney, Agent, or Firm*—Gunn & Lee PC

(57) ABSTRACT

A method and system for implementing magnetostrictive sensor techniques for the nondestructive evaluation of pipeline structures. The system consists of a magnetostrictive sensor instrument unit, a data storage unit, and a plurality of magnetostrictive sensor probes are positioned on an in-line inspection vehicle. The instrumentation unit includes electronics for transmitting excitation pulses to a transmitting magnetostrictive sensor probe as well as electronics for amplifying and conditioning the signals detected by a receiving magnetostrictive sensor probe. The magnetostrictive sensor probes include both plate magnetostrictive sensors and permanent magnets which provide a DC bias magnetic field necessary for magnetostrictive sensor operation. The transmitting and receiving probes are attached to the in-line inspection vehicle by way of mechanical arms on opposing sides of the vehicle. The mechanical arms are spring loaded and are equipped with rollers which maintain the probes at approximately constant distances from the inside diameter of the pipe wall. The method involves generating pulses of shear horizontal waves of frequencies less than 200 kHz. The transmitting magnetostrictive sensor probe generates a wave that propagates in both directions around the circumference of the pipe wall from a point adjacent to the transmitting probe. Both waves are thereafter received at the receiving probe spaced 180 degrees apart from the transmitting probe. Any defect present in the pipe wall within the circumference being investigated will show up in the received signal.

14 Claims, 3 Drawing Sheets

U.S. PATENT DOCUMENTS 5,454,276 A 10/1995 Wernicke
5,456,113 A 10/1995 Kwun et al.
5,457,994 A 10/1995 Kwun et al.
5,581,037 A 12/1996 Kwun et al.
5,675,251 A 10/1997 MacLean et al.
5,864,232 A 1/1999 Laursen
5,907,100 A 5/1999 Cook
6,023,986 A 2/2000 Smith et al.
6,205,859 B1 * 3/2001 Kwun et al. ..... 73/579

* cited by examiner

METHOD AND APPARATUS FOR INSPECTING PIPELINES FROM AN IN-LINE INSPECTION VEHICLE USING MAGNETOSTRICTIVE PROBES

Matter enclosed in heavy brackets [ ] appears in the original patent but forms no part of this reissue specification; matter printed in italics indicates the additions made by reissue.

RELATIONSHIP TO OTHER APPLICATIONS

The present application is a continuation-in-part of U.S. patent application Ser. No. 09/519,530 filed Feb. 25, 2000, now U.S. Pat. No. 6,294,912, which is the National Phase Entry of PCT patent application Ser. No. PCT/US00/06359 filed Feb. 25, 2000, which claims the priority filing of U.S. Provisional Patent Application Ser. No. 60/124,763 filed Mar. 17, 1999.

BACKGROUND OF THE INVENTION

1. Field of the Invention

The present invention relates generally to methods and devices for the nondestructive evaluation of materials. The present invention relates more specifically to a magnetostrictive sensor based system for the inspection of pipeline structures from an in-line inspection vehicle.

2. Description of the Related Art

The use of magnetostrictive sensors (MsS) in the nondestructive evaluation (NDE) of materials has proven to be very effective in characterizing defects, inclusions, and corrosion within various types of ferromagnetic and non-ferromagnetic structures. A MsS launches a short duration (or a pulse) of elastic guided waves in the structure under investigation and detects guided wave signals reflected from anomalies such as defects in the structure. Since guided waves can propagate long distances (typically 100 ft or more), the MsS technique can inspect a significant volume of a structure very quickly. In comparison, other conventional NDE techniques such as ultrasonics and eddy current inspect only the local area immediately adjacent to the probes used. Therefore, the use of magnetostrictive sensors offers a very cost effective means for inspecting large areas of steel structures such as strands, cables, pipes, and tubes quickly with minimum support requirements such as surface preparation, scaffolding, and insulation removal. The ability to use magnetostrictive sensors with little preparation of the object under inspection derives from the fact that direct physical contact between the sensors and the material is not required.

Efforts have been made in the past to utilize magnetostrictive sensor technologies in association with the inspection of both ferromagnetic and non-ferromagnetic materials. Included in these efforts are systems disclosed in U.S. Pat. Nos. 5,456,113, 5,457,994 and 5,501,037 which are each commonly owned by the assignee of the present invention. The disclosures of U.S. Pat. Nos. 5,456,113, 5,457,1994 and 5,501,037 provide background on the magnetostrictive effect and its use in NDE and are therefor incorporated herein by reference. These efforts in the past have focused primarily on the external inspection of piping, tubing and steel strands/cables wherein the nature of the structure is such that uninterrupted internal access to the pipe wall is very limited. While these systems and their external application to longitudinal structures find significant applications, there are yet other inspection techniques structures that could benefit from the use of magnetostrictive based NDE.

BACKGROUND OF THE MAGNETOSTRICTIVE EFFECT

The nondestructive evaluation of materials using magnetostrictive sensors is based upon the magnetostrictive effect and its inverse effect. The magnetostrictive effect is a phenomenon that causes the physical dimensions of a ferromagnetic material to change slightly when the material is magnetized or demagnetized or otherwise experiences a changing magnetic field. The inverse effect is a phenomenon that causes a magnetic flux in the material to change when the material is stressed. Systems utilizing magnetostrictive sensors use the magnetostrictive effect and its inverse effect to generate and detect guided waves that travel through the ferromagnetic material.

In general, a magnetostrictive sensor consists of a conductive coil and a means for providing a DC bias magnetic field in the structure under inspection. The means for providing a bias magnetic field can include the use of either permanent magnets or electromagnets. In a transmitting magnetostrictive sensor, an AC electric current pulse is applied to the coil. The resulting AC magnetic field (a changing magnetic field) produces elastic waves (also known as guided waves) in an adjacent ferromagnetic material through the magnetostrictive effect. In the receiving magnetostrictive sensor, a responsive electric voltage signal is produced in the conductive coil when the elastic waves (transmitted or reflected from anomalies within the material) pass the sensor location, through the inverse magnetostrictive effect.

With MsS techniques, defects are typically detected by using the pulse-echo method well known in the field of ultrasonics. Since the sensor relies on the magnetostrictive behavior found in ferromagnetic materials, this technology is primarily applicable to the inspection of ferromagnetic components such as carbon steel piping or steel strands. It is also applicable, however, to the inspection of nonferrous components if a thin layer of ferromagnetic material, such as nickel, is plated or coupled onto the component in the area adjacent to the magnetostrictive sensors.

The magnetostrictive sensor technique has the advantage of being able to inspect a large area of material from a single sensor location. Such sensors have, for example, been used to accurately inspect a length of pipe or cable of significantly more than 100 feet. Further, magnetostrictive sensor techniques are comprehensive in their inspection in that the methods can detect both internal and external defects, thereby providing a 100% volumetric inspection. The techniques are also quite sensitive, being capable of detecting a defect with a cross-section less than 1% of the total metallic cross-section of cylindrical structures such as pipes, tubes, or rods. Finally, as indicated above, magnetostrictive sensor techniques do not require direct physical contact between the component surface and the sensor itself. This eliminates the need for surface preparation and permits the movement of the sensor across the surface without concern for abrasive contact.

APPLICATION TO PIPELINE STRUCTURES

Gas transmission pipelines are typical of tubular structures that regularly require inspection for defects to insure their structural integrity and their safe operation. The primary traditional tool utilized to inspect such pipelines is referred to an in-line inspection (ILI) vehicle or pig that is equipped with an inspection device and travels down the length of the pipeline inside the conduit. The detection of corrosion metal loss is typically accomplished using devices based on the magnetic flux leakage (MFL) technique. Magnetic flux leakage devices work well, although they are heavy and difficult to handle. In most instances, MFL devices lack the flexibility to accommodate different pipe diameters, and as such different devices are needed for each pipeline diameter to be inspected.

For the detection of cracks such as stress corrosion cracking (SCC) that occur in the longitudinal direction of a pipeline, devices based on the ultrasonic techniques are frequently used. Ultrasonic devices, such as those developed by British Gas, employ an array of wheel type piezoelectric transducers to couple an ultrasonic wave into and out from the pipe wall without the need of a liquid couplant. Such ultrasonic devices work reasonably well but tend to be very expensive to build and operate. Because of the high inspection costs associated with ultrasonic devices, the gas pipeline industry has devoted much research to finding a more economical approach to pipeline inspection.

One current direction of the active research and development in the gas pipeline industry focuses on the use of electromagnetic acoustic transducers (EMATs) which require no liquid couplant to convey a signal to and from the investigated material. Other research and development efforts are focusing on systems that use the high-pressure gas as a coupling medium to convey the interrogating signal. Recent applications of plate magnetostrictive sensor probes have shown promise in a variety of structural geometrys. In addition to the benefits associated with not requiring a liquid couplant, magnetostrictive sensor probes offer further advantages in that: (1) they can detect both corrosion metal loss and stress-corrosion cracking as well as coating disbond; (2) they are simple in design, lightweight, and easy to handle; (3) they can readily accommodate different pipeline diameters; and (4) they are economical to manufacture and operate.

A plate magnetostrictive sensor operates by using the magnetostrictive force as described above and thus differs from EMATs which are based on the Lorentz force. EMATs used on ferromagnetic steel also encounter the magnetostrictive force and can utilize the magnetostrictive force for wave generation and detection. However, EMATs use a meandering coil type design where the adjacent coil lines are separated by a half wave length distance in order to reinforce a localized excitation and detection in the material. In order to maintain a reasonable sensor size, EMATs are designed to operate at relatively high frequency (typically over 500 kHz). A few EMAT sensors have been developed that are capable of operating down to about 250 kHz.

Plate type magnetostrictive sensor probes are designed quite differently from EMAT based sensors. Plate type magnetostrictive sensors consist of a coil wound on a U-shaped core. Typically the coil is 50 to 100 turns and the U-shaped core is 6 to 10 inches long. The plate type magnetostrictive sensor probes typically operate below 200 kHz. Because of the unique sensor design and low frequency operation, the magnetostrictive probes have good sensitivity, are more tolerant to lift off, and have a longer inspection range than generally available EMATs.

Efforts at providing methods and devices for detecting defects in pipelines have included the following:

U.S. Pat. No. 5,907,100 issued to Cook on May 25, 1999 entitled Method and System for Detecting and Displaying Defects in Piping. This patent describes a typical EMAT sensor based device wherein an EMAT transmitter sends an ultrasonic wave through the pipe wall and receives a reflected ultrasonic signal from a defect in the pipe.

U.S. Pat. No. 5,675,251 issued to MacLean et al. on Oct. 7, 1997 entitled Device and Method for Inspection of Pipelines. This patent describes a plurality of housing units that are generally spherical in shape for inspecting the integrity of water distribution pipelines. The housing units are connected by flexible connections that permit movement of the inspection device easily through bends and constricted areas within the pipeline.

U.S. Pat. No. 4,439,730 issued to Kaufmann on Mar. 27, 1984 entitled Nondestructive Inspection Apparatus and Method Utilizing Combined Inspection Signals Obtained from Orthogonal Magnetic Fields. This patent describes one of the above mentioned magnetic flux leakage (MFL) techniques currently utilized in conjunction with in-line inspection vehicles. The process described involves establishing a steady magnetic flux field through an area in a first direction and then passing a magnetic flux field through the same area in an orthogonal direction.

U.S. Pat. No. 5,454,276 issued to Wernicke on Oct. 3, 1995 entitled Multidirectional Magnetic Flux Pipe Inspection Apparatus and Method. This patent likewise describes a magnetic flux leakage (MFL) technique device positioned on a pipeline inspection pig having a drive mechanism and magnetic field generators. The method anticipates a helical progression through the pipeline so as to generate a grid of helical sensor signals from a plurality of MFL sensors.

U.S. Pat. No. 5,864,232 issued to Laursen on Jan. 26, 1999 entitled Magnetic Flux Pipe Inspection Apparatus for Analyzing Anomalies in a Pipeline Wall. This patent describes yet another magnetic flux leakage technique device whose functional principles are schematically explained in FIG. 2 of the patent. A variety of mechanisms for maintaining the sensors in close proximity to the pipeline wall are described. Wear plates and wear pads mounted on the top of the sensor body are described for reducing wear on the contacting sensor.

U.S. Pat. No. 5,581,037 issued to Kwun et al. on Dec. 3, 1996 entitled Nondestructive Evaluation of Pipes and Tubes Using Magnetostrictive Sensors. This patent describes an application of magnetostrictive technologies and techniques as applied externally on a longitudinal body such as a pipe tube or other cylindrical shell. The system anticipates the establishment of longitudinally directed mechanical waves within the pipeline which are detected at distant magnetostrictive sensors.

U.S. Pat. No. 6,023,986 issued to Smith et al. on Feb. 15, 2000 entitled Magnetostrictive Flux Leakage Inspection Technique for Pipelines. This patent describes yet another MFL system that includes an inertial navigation system and a global positioning system. The basic structure for establishing a magnetic flux leakage sensor is shown in FIG. 1 of the patent where magnetic coupling to the wall of the pipeline is made by way of pliable steel brushes.

As indicated above, it would be desirable to benefit from the advantages that magnetostrictive sensor probes have over EMAT and MFL based sensor probes within a structure and with a technique that traverses the internal space of a gas pipeline for inspection purposes. It would be advantageous to be able to utilize plate magnetostrictive sensor probes as are currently externally applied to materials under investigation to an in-line transport device capable of moving the sensors down the length of a gas pipeline or the like.

It would therefore be desirable to implement magnetostrictive sensor techniques in conjunction with pipeline structures in a manner similar to, and with the accuracy of, such systems utilized externally in conjunction longitudinal cylindrical structures. It would be desirable if an inspection of pipeline structures could be carried out in an efficient manner that did not require access to the outside surface of the pipeline. Such a magnetostrictive sensor system would be able to investigate long lengths of a pipeline structure and would provide a cost effective global inspection of the structure.

SUMMARY OF THE PRESENT INVENTION

It is therefore an object of the present invention to provide a sensor device for implementing magnetostrictive based NDE in association with pipeline structures in order to evaluate the condition of the structure and determine the presence of anomalies indicative of fracture, deteriorations, and the like.

It is a further object of the present invention to provide magnetostrictive sensor devices appropriate for use in conjunction with the inspection of pipeline structures that is capable of transmitting and receiving guided waves within the pipeline wall structures and generating signals representative of the characteristics of such waves appropriate for the analysis and detection of anomalies therein.

It is a further object of the present invention to provide magnetostrictive sensor devices appropriate for use in conjunction with the inspection of pipeline structures that progressively inspect the circumference of the pipeline structure for anomalies, corrosion, fractures, and the like in a cost effective manner.

It is a further object of the present invention to provide a method for the inspection of pipeline structures that includes the use of a magnetostrictive sensor specifically adapted for directing guided waves into the pipeline wall and detecting such waves as may be reflected from anomalies within the pipeline wall.

It is a further object of the present invention to provide a method and apparatus for the nondestructive evaluation of pipeline structures utilizing magnetostrictive sensors that are capable of progressively investigating large volumes of the pipeline structures without access to the external surface area of the pipeline.

In fulfillment of these and other objectives, the present invention provides a method and system for implementing magnetostrictive sensor techniques for the nondestructive evaluation of pipeline structures. The system consists of a magnetostrictive sensor instrument unit, a data storage unit, and a plurality of magnetostrictive sensor probes that are positioned on an in-line inspection vehicle. The instrumentation unit includes electronics for transmitting excitation pulses to a transmitting magnetostrictive sensor probe as well as electronics for amplifying and conditioning the signals detected by a receiving magnetostrictive sensor probe. The magnetostrictive sensor probes include both plate magnetostrictive sensors and permanent magnets which provide a DC bias magnetic field necessary for magnetostrictive sensor operation. The transmitting and receiving probes are attached to the in-line inspection vehicle by way of mechanical arms on opposing sides of the vehicle. The mechanical arms are spring loaded and are equipped with rollers which maintain the probes at approximately constant distances from the inside diameter of the pipe wall. The method involves generating pulses of shear horizontal waves of frequencies less than 200 kHz. The transmitting magnetostrictive sensor probe generates a wave that propagates in both directions around the circumference of the pipe wall from a point adjacent to the transmitting probe. Both waves are thereafter received at the receiving probe spaced 180 degrees apart from the transmitting probe. Any defect present in the pipe wall within the circumference being investigated will show up in the received signal.

DETAILED DESCRIPTION OF THE PREFERRED EMBODIMENT

Figure 1:
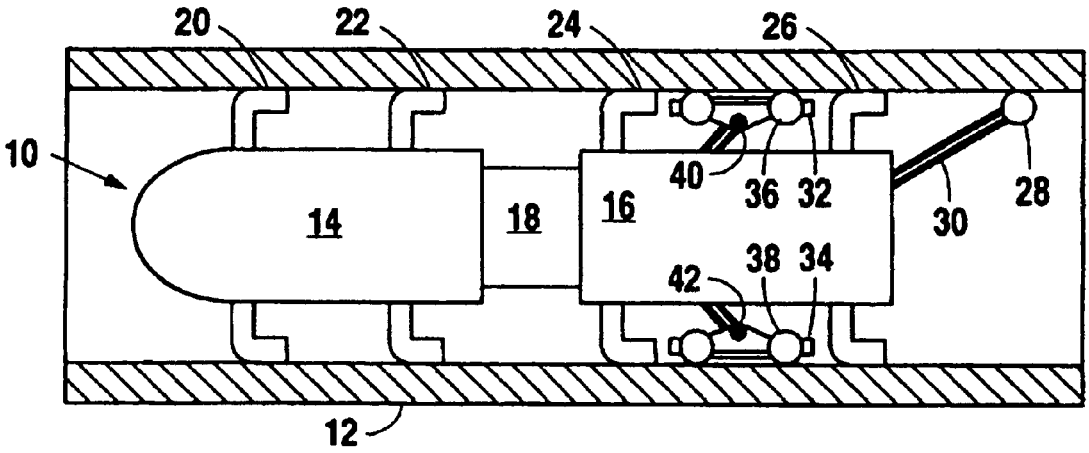
FIG. 1 is a longitudinal cross section of a pipeline carrying the in-line inspection vehicle of the present invention.

Reference is made first to FIG. 1 for a description of the structure of a preferred embodiment of the present invention shown in longitudinal cross section and positioned within a typical gas pipeline. In FIG. 1, pipeline wall 12 may be any of a number of standard sized gas pipelines, an example of which might be a 24 inch outside diameter, 0.562 inch thick pipe wall. In-line inspection vehicle 10 is comprised primarily of battery section 14 and sensor/instrument section 16. Sections 14 and 16 are connected together by a flexible coupling 18 which provides the necessary power connections between the sections and permits movement of in-line inspection vehicle 10 through bends and curves in pipeline 12.

In-line inspection vehicle 10 is propelled down the length of pipeline 12 by the pressurized gas carried through the pipeline. This propulsion is accomplished by use of a number of flexible cups 20, 22, 24 and 26 that are positioned in spaced arrangement on battery section 14 and instrument section 16. These flexible cups provide a loose seal against the inside diameter of the pipeline wall in a manner that allows the pressurized gas to push the vehicle down the pipeline. The speed of the vehicle may of course be controlled by varying the pressure behind the vehicle.

Sensor/instrument section 16 retains the electronics and sensors necessary for directing the interrogating waves into the pipe wall and receiving such reflected or transmitted waves from the pipe wall for recording. It is anticipated that this stand alone vehicle would generate and record signal data that would later by analyzed after the vehicle is removed from the pipeline. Flexibly attached to sensor/instrument section 16 are movable mechanical arms 40 and 42 which are spring loaded and are equipped with rollers 36 and 38 that maintain magnetostrictive sensor probes 32 and 34 at approximately a constant distance from the inside diameter of pipeline wall 12. Also shown in FIG. 1 is a rolling odometer 28 positioned on a third mechanism arm 30 which tracks and records the linear displacement of the in-line inspection vehicle along the length of the pipe.

Figure 2:
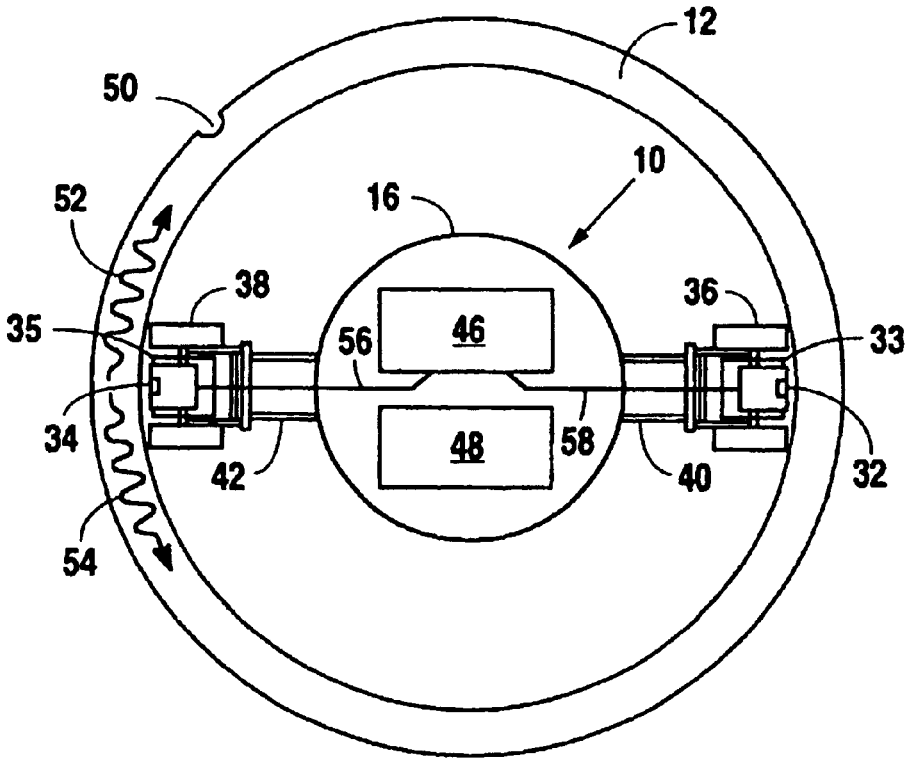
FIG. 2 is a transverse cross section of the pipeline shown in FIG. 1 disclosing in greater detail the positioning of the magnetostrictive sensors adjacent the inside diameter of the pipe wall.

Reference is now made to FIG. 2 for a detailed description of a transverse view of the in-line inspection vehicle 10 shown in FIG. 1. Particular focus in FIG. 2 is made on the sensor/instrument section 16. Within sensor/instrumentation section 16 are positioned magnetostrictive sensor instrument unit 46 and data storage unit 48. On opposing sides of sensor/instrument section 16 are positioned mechanical arms 40 and 42 which terminate in rollers 36 and 38 which make contact with the inside diameter of pipeline wall 12. Positioned in association with the end of mechanical arms 40 and 42 are plate magnetostrictive sensors 32 and 34. As indicated above, the sensors themselves are positioned so as to be held at a constant distance separated from the pipeline wall, which in the preferred embodiment constitutes a distance of approximately 0.1 inches.

Signal lines 56 and 58 connect magnetostrictive sensor instrument unit 46 to each of the magnetostrictive sensors 32 and 34. In the embodiment shown in FIG. 2 magnetostrictive sensor 34 is configured to be the transmitting sensor while sensor 32 is configured to be the receiving sensor. It is understood by those skilled in the art that the structure of these sensors may be identical and that their function is determined by the instrumentation control electronics. Associated with magnetostrictive sensors 32 and 34 are permanent bias magnets 33 and 35. These bias magnets 33 and 35 are shown in dashed outline in FIG. 2 for clarity. The manner in which bias magnets 33 and 35 are positioned in conjunction with magnetostrictive sensors 32 and 34 is described in more detail below with respect to FIG. 7.

The process of inspecting a circumferential section of pipe wall involves generating a pulse of shear horizontal (SH) waves at the transmitting magnetostrictive sensor probe 34. In the preferred embodiment these waves have frequencies of no more than 200 kHz. The actual (optimal) wave frequency is adjusted before launching the in-line inspection vehicle and depends upon factors associated with the specific pipeline under inspection. The factors that are considered in selecting the wave frequency include the wave attenuation per circumference of the pipe section, the beam spreading properties of the pipeline material, and the presence of higher mode shear horizontal waves. Optimum frequency selection involves achieving a detected signal that minimizes the signal to noise ratio and yet accurately detects defects above a critical size. As indicated above, magnetostrictive sensors in general have been shown to provide interpretable output signals when the input wave frequency is less than 200 kHz.

Once transmitting magnetostrictive probe 34 generates the pulsed wave in pipe wall 12, the wave propagates in both clockwise and counter-clockwise directions. In FIG. 2 these wave propagations are indicated at 52 and 54. Since receiving probe 32 is positioned 180 degrees apart from transmitting probe 34, generated waves 52 and 54 propagating in opposite directions arrive at receiving probe 32 at the same time. As a result, the two opposing travelling waves 52 and 54 add constructively producing a single large amplitude signal. The initially generated waves 52 and 54 continue to travel around the pipe circumference until their energies are dissipated. This continued circumferential wave motion produces signals at regular intervals that are equal to the transit time for the shear horizontal waves to travel around the full circumference. Any defects or anomalies, such as defect 50 shown in FIG. 2, encountered along the way, reflect a portion of the transmitted wave in a manner that provides a new signal component received at magnetostrictive sensor probe 32.

Figure 6:
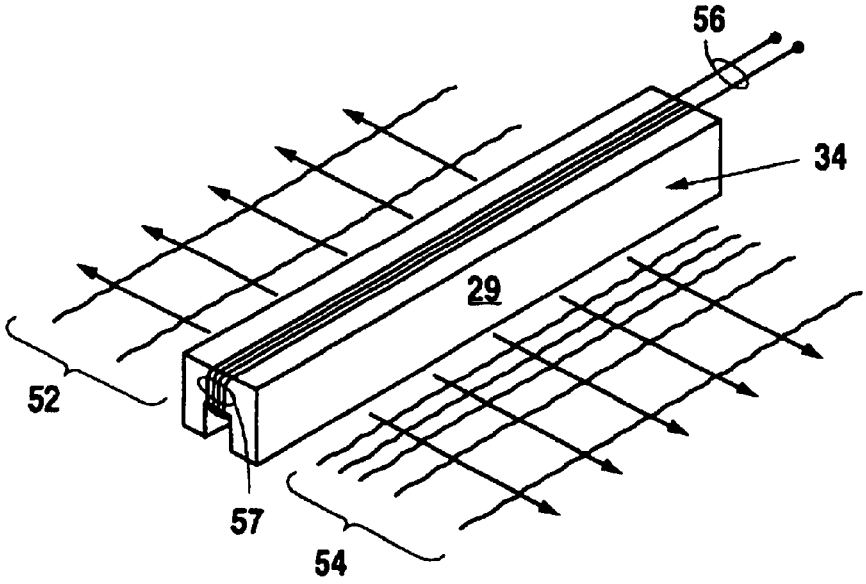
FIG. 6 is a perspective view of the magnetostrictive sensor utilized as a transmitting sensor in the system of the present invention.
Figure 7:
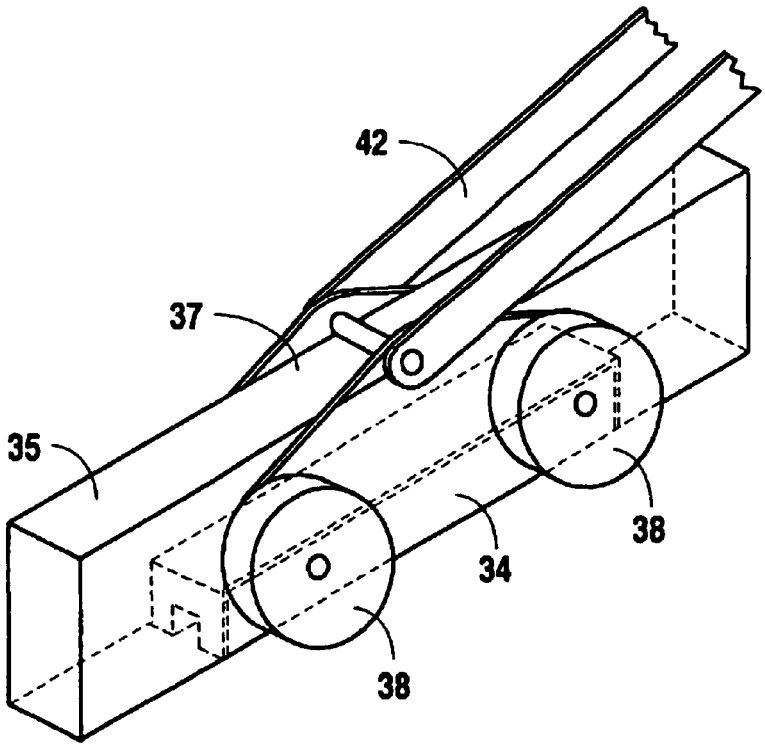
FIG. 7 is a detailed perspective view of the sensor shown in FIG. 6 mounted on a moveable carriage appropriate for use in conjunction with the system of the present invention.

Reference is made to FIGS. 6 and 7 for a more detailed description of the structure and function of the plate type magnetostrictive sensors utilized in the present invention. The novel structure of magnetostrictive sensor 34, as shown in FIG. 6, may be utilized as either a transmitter sensor or a receiver sensor. In FIG. 6, magnetostrictive sensor 34 is shown as it might be implemented as a transmitter. In the preferred embodiment, magnetostrictive sensor 34 is comprised of a plurality of U-shaped cross-section cores stacked in a lengthwise direction to form sensor core 29 having a longitudinal axis that is long in comparison to the dimensions of its cross-section. Sensor core 29 in the preferred embodiment may be made from a stack of U-shaped ferrites, transformer steel sheets, milled steel or other ferromagnetic material. Sensor core 29 may have other shapes; however, U-shaped or E-shaped core elements have been found to be more efficient. If an E-shaped core is used, a transmitter may be located on one part of the E with a receiver function carried out by the other part of the E.

Surrounding sensor core 29 is wire coil 57. The number of turns for coil 57 is dependent upon the driving current and the magnetic permeability of sensor core 29 and may be varied as is well known in the art. Wire coil 57 terminates with signal line 56 which connects to sensor instrument unit 46 as described above.

As indicated above plate type magnetostrictive sensor 34 generates shear horizontal waves shown at 52 and 54 in FIG. 6. These opposite traveling waves, also as shown in FIG. 2, provide the necessary interrogating signal that is then received either directly or with reflected components at the receiving magnetostrictive sensor.

FIG. 7 is a detailed perspective view of one of the two carriage assemblies shown associated with in-line inspection vehicle 10 of the present invention. The carriage assembly shown in FIG. 7 may be either of the two oppositely positioned assemblies shown generally in both FIG. 1 and FIG. 2. The end of mechanical arm 42 pivotally retains carriage element 37. In the preferred embodiment carriage element 37 is a frame that supports a number of wheels 38 that permit movement of the carriage along the inside surface of the pipe wall, and at the same time serve to maintain the spacing between the magnetostrictive sensor and the pipeline wall as described above. In FIG. 7, magnetostrictive sensor 34 is surrounded by bias magnet 35 in the longitudinal direction. Wire coil 57 and signal line 56 are not shown in FIG. 7 for clarity. Carriage element 37 retains bias magnet 35 and magnetostrictive sensor 34 in fixed relationship to each other and in fixed spaced relationship to the inside surface of the pipe wall. Movement of the carriage assembly is shown in FIG. 7 with arrows in either direction along the longitudinal axis of magnetostrictive sensor 34. The pivot point in carriage element 37 permits the inspection vehicle of the present invention to be utilized in conjunction with a variety of pipeline diameters. It is anticipated that the system of the present invention, including the instrumentation section and sensor sections shown in FIG. 2, could be incorporated into a unit that is attachable to any of a number of different already known in-line inspection vehicles or transport mechanisms. This versatility facilitates the low cost implementation of the system of the present invention in that any of a number of transport vehicles may be utilized with the basic system structure shown in FIG. 2 and in detail in FIG. 7.

Figure 3:
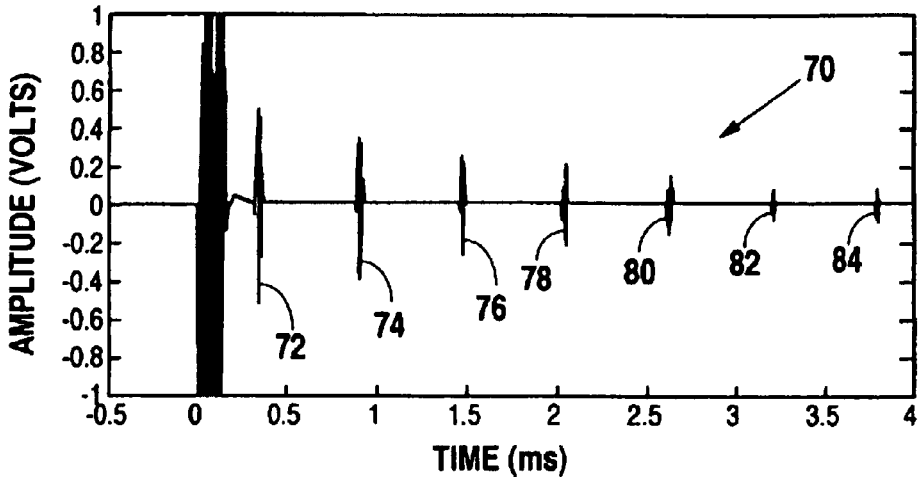
FIG. 3 is signal plot showing an example of detected signals from a generated wave utilizing the system and method of the present invention.
Figure 4:
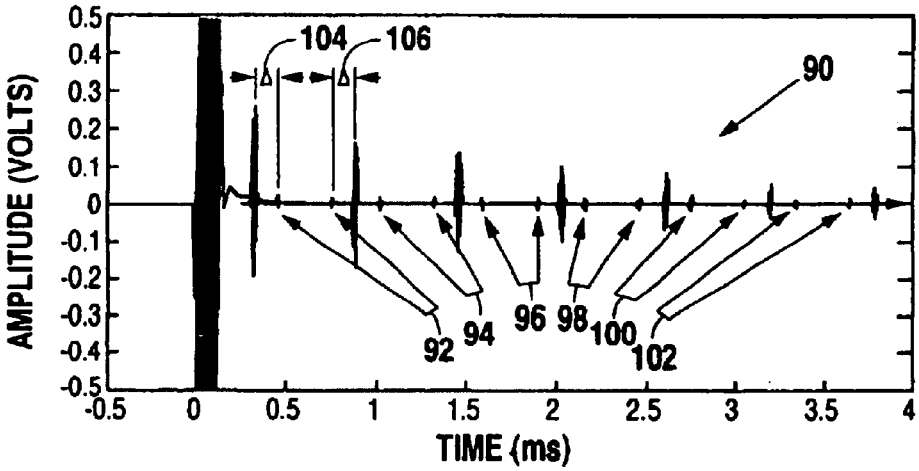
FIG. 4 is a signal plot of the same pipeline section shown in FIG. 3 but with a defect established in the pipe wall.
Figure 5:
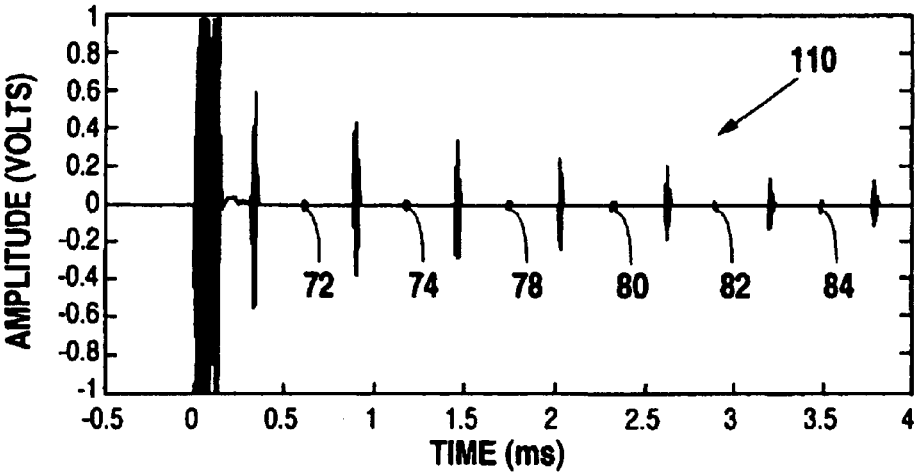
FIG. 5 is a signal plot showing a characteristic form where the defect detected is located at a midpoint between the transmitting and receiving probes.

Reference is now made to FIGS. 3 through 5 for examples of signals received using the method and system of the present invention. If a defect (such as 50 in FIG. 2) is present in the pipe wall, "defect signals" will occur between adjacent primary signals produced by the initial waves traveling circumferentially around the pipe. FIG. 3 provides an example of a detected signal from just the initial transmitted waves generated as described above. In the example shown in FIG. 3, the detected signal is from waves travelling in a 24 inch outside diameter, 0.562 inch thick wall pipe. The long inspection range characteristic of plate magnetostrictive sensor probes permits the entire pipe circumference to be inspected using only the single pair of transmitting/receiving probes described above. Many other devices require an array of sensors (see Prior Art described above) in order to accomplish the same circumferential inspection.

Signal 70 disclosed in FIG. 3 is comprised of a sequence of pulse components 72 through 84 that represent only the initial interrogating signals propagated through the pipe wall. Signal element 72, as an example, comprises the response of the magnetostrictive sensor acting as the receiving sensor when the two wave pulses traveling in opposite directions arrive at the sensor at the same time. As indicated above, because the transmitter and receiving sensors are located at 180 degrees from each other, the two waves arrive at the same time thus adding their amplitudes at the receiving sensor. The gradual decrease in amplitude shown in FIG. 3 is of course a result of the attenuation of the waves and the divergence of the wave beam as they repeatedly circle the circumference of the pipe wall.

Again, as indicated above, if a defect is present in the pipe wall, the defect signals will be discernable between two adjacent primary signals produced by the initial waves revolving around the pipe. An example of defect signals is given in FIG. 4 which was obtained from the same pipe identified above with FIG. 3 after inducing a notch in the pipe wall such as that shown in FIG. 2. Because the waves generated propagate in both directions from the point adjacent to the transmitting sensor, a single defect produces two distinct defect signals, one caused by the wave propagating in a clockwise direction, and the other caused by the wave propagating in the counter-clockwise direction. The time separation 104 between a defect signal and the nearest signal of the initial wave revolving around the pipe is equal to 2d/V where d is the distance between the defect and the nearest sensor probe (either transmitting or receiving) and V is the shear-horizontal wave velocity in steel.

Signal 90 in FIG. 4 is seen to comprise a plurality of defect signals 92 through 102, again because of the continued travel of the waves around the circumference of the pipe wall gradually being attenuated over time. The first intermediate defect signal in the pair of defect signals 92 is a result of the first of the two initial waves encountering the defect on "its side" of the pipe wall circumference. The second of the two defect signals in defect pair 92 is a result of the second initial wave encountering the defect at a later time than the first of the initial waves. From this it can be seen that time difference 104 will be equal to time difference 106 shown in FIG. 4.

When the defect is located at a midpoint between the transmitting and receiving probes, the two defect signals converge to the midpoint between the two adjacent initial wave signals as illustrated in FIG. 5. In signal 110 shown in FIG. 5, defect signals 112 through 122 are actually the constructive convergence of the two defect signals which were separated in FIG. 4. If the defect is located at exactly the center point between the two sensor probes, the defect signals will fully merge into a single signal.

The benefits of utilizing the inspection method described above with the apparatus identified are many. The system is simple in construction because it utilizes only a single transmitting probe and a single receiving probe. As such, the system can readily accommodate different pipeline diameters with little or no alteration to the basic device structure. Under the design shown, one system structure can be utilized to inspect pipelines ranging from 10 to 48 inches in outside diameter. In addition, the initial wave signals allow the wave attenuation to be determined which in turn can be utilized to detect a coating disbond area which will reflect a lower wave attenuation. It is also possible to utilize the ratio between the defect signal amplitude and the initial wave signal amplitude to determine and characterize the defect size. The initial wave signals thus provide a self calibration wherein the amplitude of various signal elements are indicative of the element's source.

The manner in which defect signals are exposed in pairs (when the defect is not at the center point between the transmitter and receiver probes), allows confirmation of the source of the signal component as a defect rather than an extraneous signal features. One shortcoming of the inspection technique and method described above, relates to the inability to identify the exact circumferential location of the defect because two defect signals are generated from a single defect. Reference to FIG. 4 confirms that it is not possible to determine which of the two simultaneously generated waves first encounters the defect in the pipe wall. The time differential shown in FIG. 4 reflects a circumferential position apart from the transmitting probe in either the clockwise or counter-clockwise direction but cannot identify which of the two directions it reflects.

Exact defect location can be determined by generating a transmitted wave in a single direction (instead of both directions simultaneously) and by employing two transmitting and receiving probe pairs. This of course requires additional complexity in instrumentation that would control signal timing and direction. These additional control factors further complicate analysis of the signal data that is received. In most instances, it is not worth the additional complexity to obtain the exact circumferential location. In most cases pipeline industries are looking for an in-line inspection device that can identify the existence of a defect at a particular linear displacement along the length of the pipeline. The odometer of the present invention provides such linear data while the mangetostrictive sensor probes provide the identification of a defect in a specific circumferential ring of pipe wall.

It should further be noted that due to the dead zone associated with the magnetostrictive sensors the inspection approach described leaves a small section of the pipe circumference uninspected. It may be desirable in order to cover the entire circumference to provide a second set of magnetostrictive sensor probes with associated instrumentation of the in-line inspection vehicle. The magnetostrictive sensor probes of the second set would be oriented at a different angular position from that of the first set. Although the angle could be any angle that displaces the sensors sufficiently one from the other, an optimal arrangement might have the second sensor pair oriented orthogonally to the first sensor pair. The signal data from the second set of probes would not only eliminate the uninspected area (associated with the pipe wall immediately adjacent the initial set of probes) but would also serve as a backup and confirmation of the data acquired from the first set. Comparisons could be made between the two sets of data to confirm a defect signal as not originating from a non-defect source.

Although a description of a preferred embodiment of the apparatus and method of the present invention has been provided, it is anticipated that variations in the manner in which the basic sensor structure of the present invention may be utilized are possible. No optimal dimensions for the sensor structure described have been identified as such would be dependent upon the geometry of specific pipeline structures to be investigated. It is anticipated that sensors of a variety of sizes operating at a variety of frequencies could be utilized depending upon the requirements of the environment of investigation. In general, the basic structure of the sensors described in the present invention may be utilized wherever ferromagnetic pipeline material is utilized. It is anticipated that other applications of the basic sensor structure described herein will be discerned by those skilled in the art of nondestructive evaluation of pipeline materials.

We claim:

1. A system for the non-destructive evaluation of a pipeline structure *having an interior, said system* comprising:

a mobile in-line transport vehicle for [translational] *longitudinal* movement through the interior of said pipeline structure*, said vehicle having a sensor/instrument section and a battery section mounted thereon*;

a linear displacement sensor positioned on said vehicle for generating a signal indicative of said [translational] *longitudinal* movement of said vehicle through the interior of said pipeline structure;

[at least one] *a transmitting* magnetostrictive sensor [positioned on said vehicle,] *and a receiving magnetostrictive sensor flexibly attached to said sensor/instrument section, each of* said magnetostrictive sensor*s* comprising[;]*:* an elongated core *parallel to said longitudinal movement*, said core having a length much longer than dimensions of its cross-section;

a coil wound around said length of said elongated core; and*,* means for establishing a bias magnetic field proximate to said elongated core;

wherein said [at least one] magnetostrictive [sensor is positioned on] *sensors are flexibly attached to* said *sensor/instrument section mounted on said* transport vehicle *and are positioned* so as to maintain a generally constant close-spaced position [with respect to] *on opposite sides of* an inside wall of said pipeline structure as said transport vehicle is moved through the interior of said pipeline structure*; and,*

*said battery section mounted on said vehicle being electronically connected to said sensor/instrument section by a flexible coupling.*

[2. The system of claim 1 wherein said at least one magnetostrictive sensor is operable as both a transmitting magnetostrictive sensor and a receiving magnetostrictive sensor.]

3. The system of claim 1 wherein said [at least one magnetostrictive sensor comprises at least one transmitting magnetostrictive sensor and at least one] receiving magnetostrictive sensor[, said at least one receiving sensor] *is* positioned at a fixed separation from said at least one transmitting *magnetostrictive* sensor.

4. The system of claim 1 wherein said mobile in-line transport vehicle further comprises at least one spring-loaded mechanical arm extending from said transport vehicle to a point of movable contact with said pipeline structure, [said] at least one *of said* magnetostrictive sensor positioned on said at least one mechanical arm proximate to said pipeline structure.

5. The system of claim 4 wherein said in-line transport vehicle further comprises a plurality of wheels positioned on said at least one mechanical arm and contacting said pipeline structure so as to permit said [translational] *longitudinal* movement through the interior of said pipeline structure by said transport vehicle.

[6. The system of claim 1 where in said elongated core of said at least one magnetostrictive sensor is oriented such that a longitudinal axis of said core is parallel with a longitudinal axis of said pipeline structure and is therefore oriented in the direction of said translational movement of said transport vehicle.]

7. The system of claim 1 wherein said means for establishing a bias magnetic field comprises a permanent magnet positioned adjacent to said elongated core of [said at least one] *the* magnetostrictive sensor.

8. The system of claim 1 wherein said in-line transport vehicle further comprises a spring-loaded mechanical arm extending from said transport vehicle to said pipeline structure and wherein said linear displacement sensor is positioned on said mechanical arm in movable contact with said pipeline structure so as to track said [translational] *longitudinal* movement of said transport vehicle.

9. The system of claim 1 wherein said in-line transport vehicle further comprises electronic instrumentation for generating an interrogating signal through said [at least one] *transmitting* magnetostrictive sensor, receiving a return signal through said [at least one] *receiving* magnetostrictive sensor, receiving said signal indicative of said [translational] *longitudinal* movement of said vehicle from said linear displacement sensor, and recording said signals in a memory means.

10. A method for the non-destructive evaluation of a pipeline structure comprising the steps of:

positioning at least one transmitting magnetostrictive sensor adjacent to an inside wall surface of said pipeline structure;

establishing a bias magnetic field adjacent said at least one transmitting magnetostrictive sensor and within a volume of a wall of said pipeline structure;

positioning at least one receiving magnetostrictive sensor adjacent to an *opposite* inside wall surface *from said at least one transmitting magnetostrictive sensor* of said pipeline structure;

establishing a bias magnetic field adjacent *to* said at least one receiving magnetostrictive sensor and within a volume of a wall of said pipeline structure;

generating a pulsed signal and delivering said pulsed signal to said transmitting magnetostrictive sensor, said transmitting magnetostrictive sensor thereby generating a shear horizontal wave in said wall of said pipeline structure;

receiving said shear horizontal wave and any reflected waves deriving therefrom, at said receiving magnetostrictive sensor, said receiving [a] magnetostrictive sensor generating a received signal having signal elements characterizing said shear horizontal wave and any reflected waves deriving therefrom; [and]

*moving said at least one transmitting magnetostrictive sensor and said at least one receiving magnetostrictive sensor in a longitudinal direction through the interior of said pipeline structure; and,* identifying anomalous elements within said received signal, said anomalous elements indicative of known and unknown anomalies in said wall of said pipeline, said at least one transmitting and receiving magnetostrictive sensors having an elongated core *positioned parallel to an elongated axis of said pipeline structure* with a length much longer than dimensions of its cross section and a coil wound around said length of said elongated core.

11. The method of claim 10 wherein said steps of positioning at least one transmitting magnetostrictive sensor and positioning at least one receiving magnetostrictive sensor, comprise positioning said sensors [in an opposing configuration within said pipeline structure along a diameter] *180 degrees apart about an interior cross-section* of said pipeline structure.

12. The method of claim 10 wherein said step of generating a pulsed signal comprises generating a signal having a frequency of less than 200 kHz.

[13. The method of claim 10 further comprising the step of moving said at least one transmitting magnetostrictive sensor and said at least one receiving magnetostrictive sensor in a longitudinal direction through the interior of said pipeline structure.]

14. The method of claim [13] *10* further comprising the step of positioning at least one linear displacement sensor adjacent to and in contact with an inside wall surface of said pipeline structure.

15. The method of claim 10 further comprising the step of storing said received signal and said signal indicative of said [translational] *longitudinal* movement in a memory device for later retrieval and analysis.

16. The method of claim 10 wherein said step of identifying anomalous elements within said received signal comprises the step of comparing said received signal with a benchmark signal previously obtained and recorded in association with an inspection of said pipeline structure.

17. The method of claim 10 wherein said step of identifying anomalous elements within said received signal comprises identifying occurrence within said received signal wherein an amplitude of said signal exceeds a predefined range.

* * * * *